United States Patent [19]

Alagy et al.

[11] Patent Number: 4,973,777
[45] Date of Patent: Nov. 27, 1990

[54] PROCESS FOR THERMALLY CONVERTING METHANE INTO HYDROCARBONS WITH HIGHER MOLECULAR WEIGHTS, REACTOR FOR IMPLEMENTING THE PROCESS AND PROCESS FOR REALIZING THE REACTOR

[75] Inventors: Jacques Alagy, Charbonnieres; Christian Busson, Dardilly; Michel Fouquet, Oullins, all of France

[73] Assignee: Institut Francais Du Petrole, Rueil-Malmaison, France

[21] Appl. No.: 186,826

[22] Filed: Apr. 27, 1988

Related U.S. Application Data

[63] Continuation-in-part of Ser. No. 927,980, Nov. 7, 1986, Pat. No. 4,926,001.

[30] Foreign Application Priority Data

| Nov. 8, 1985 | [FR] | France | 857614 |
| Mar. 18, 1986 | [FR] | France | 8603970 |
| Jun. 23, 1986 | [FR] | France | 8609168 |
| Apr. 28, 1987 | [FR] | France | 87/06.064 |

[51] Int. Cl.$^5$ ............................................. C07C 2/00
[52] U.S. Cl. ........................... 585/403; 585/415; 585/500; 585/537; 585/539; 585/636; 585/943
[58] Field of Search ............... 585/403, 415, 500, 537, 585/539, 636, 943

[56] References Cited

U.S. PATENT DOCUMENTS

| 1,880,189 | 9/1932 | Snelling | 585/500 X |
| 1,905,520 | 4/1933 | Steigerwald | 585/943 X |
| 1,988,873 | 1/1935 | Linch et al. | 585/943 X |
| 2,061,598 | 11/1936 | Smith et al. | 585/500 |
| 2,875,148 | 2/1959 | Scofield | 585/943 X |
| 3,093,697 | 6/1963 | Kasbohm et al. | 585/539 X |
| 3,156,734 | 11/1964 | Happel | 585/539 X |
| 3,236,906 | 2/1966 | Margiloff | 585/911 |
| 4,876,409 | 10/1989 | Leyshon et al. | 585/500 |

FOREIGN PATENT DOCUMENTS

| 670240 | 9/1963 | Canada | 585/500 |
| 735978 | 6/1966 | Canada | 585/500 |
| 261267 | 11/1926 | United Kingdom | 585/500 |
| 364144 | 12/1931 | United Kingdom | 585/943 |

*Primary Examiner*—Patrick P. Garvin
*Assistant Examiner*—George R. Fourson
*Attorney, Agent, or Firm*—Millen, White & Zelano

[57] ABSTRACT

A process for thermally converting methane e.g., at 1,000°–1,300° C. into hydrocarbons with higher molecular weights, especially ethylene comprises circulating a gas containing methane in ceramic channels (11) grouped in rows which cover at least a part of the reactor (1) length, parallel to its axis. At the reaction temperature, the temperature variation is kept at less than 20° C. The rows of channels form multiple plates (4) which are not adjacent to one another and which define tight spaces (17) in which are housed the electric heating (5, 22) means that heat the channel plates in a first zone (9) through successive, independent cross sections substantially perpendicular to the axis of the reactor and substantially parallel to the plane of the plates. Means for heating, servocontrol and modulation (7, 8) regulate the heating system. At the exit of the heating zone (9), the effluent is cooled in a second zone (10) equipped with cooling means and finally collected.

23 Claims, 1 Drawing Sheet

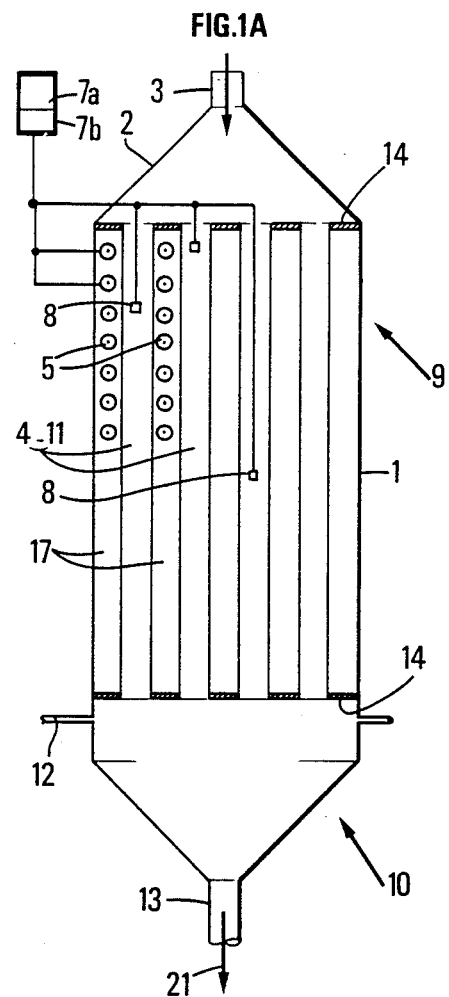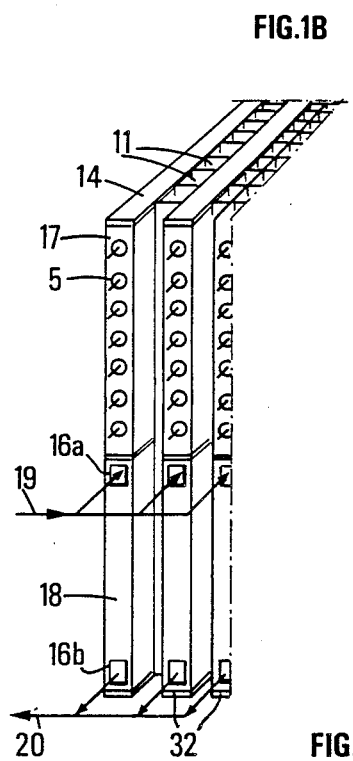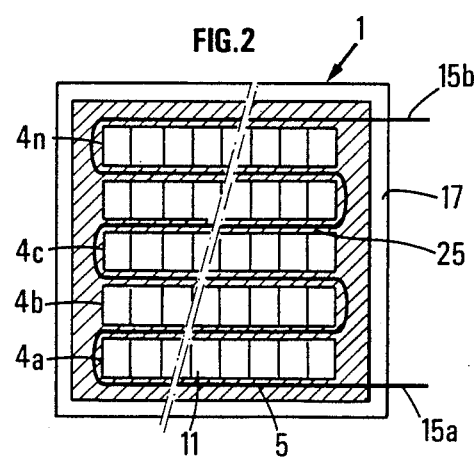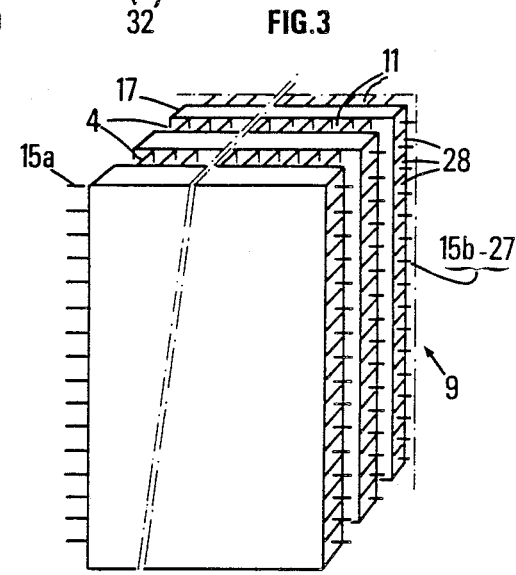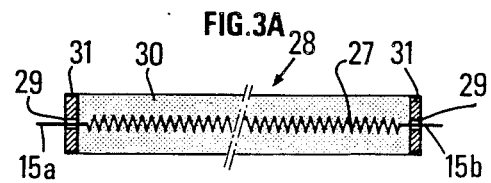

PROCESS FOR THERMALLY CONVERTING METHANE INTO HYDROCARBONS WITH HIGHER MOLECULAR WEIGHTS, REACTOR FOR IMPLEMENTING THE PROCESS AND PROCESS FOR REALIZING THE REACTOR

CROSS-REFERENCE TO RELATED APPLICATION

This application is a continuation-in-part of allowed application, Ser. No. 06/927,980 filed Nov. 7, 1986 now U.S. Pat. No. 4,926,001. Applicants claim the benefit of said earlier application under 35 U.S.C. Section 120 and also corresponding French priority application Nos. 85/16714 filed Nov. 8, 1985, 86/03970 filed Mar. 18, 1986 and 86/09168 filed Jun. 23, 1986 under 35 U.S.C. Section 119.

BACKGROUND OF THE INVENTION

This invention is a continuation-in-part of an improved process for thermally converting methane into hydrocarbons with higher molecular weights.

Among the methane sources are natural gases and refinery gases. The natural gases can either be gases associated with crude oil or not; their composition varies rather noticeably according to their origin, but they generally contain a volume percentage of methane from 60 to 95%. This methane is always associated with other higher alkanes up to and even exceeding the $C_6$. Various cryogenic processes serve to separate the gases into several fractions once the water and acid components are removed. Such fractions are: nitrogen, liquefied natural gases the propane and butane fraction of which is separated, and a fraction essentially composed of methane associated with a low amount of ethane. The latter fraction is either re-injected into the well in order to maintain the pressure which makes the crude oil rise or fed through a gas pipe line as a combustible gas, or else subjected to flaring.

Other sources of methane are refinery gases which have various origins: crude oil first still gases, hydroreforming gases, different hydrotreatment gases, thermal cracking gases, catalytic cracking gases; all these gases contain, in various proportions, methane associated with numerous other gaseous constituents, such as light hydrocarbons, nitrogen, $CO_2$, hydrogen, etc.

For example an effluent gas from a fluidized bed catalytic cracking unit comprises, after washing, about 30% by volume of methane. This gas is often fractionated by cooling under pressure, resulting in two fractions, one containing hydrogen, nitrogen, methane and a low amount of ethylene, the other fraction being composed of the main part of the initial ethylene, ethane, propane and propylene. The latter fraction can be advantageously fed into a DIMERSOL type unit, whereas the first one is fed back into the fuel-gas system of the refinery, where it is used as a fuel.

The conversion of methane into hydrocarbons with higher molecular weights is doubtlessly interesting; in far away sources of natural or associated gases, the conversion of methane into acetylene, ethylene and aromatic compounds can, using sequences of well-known processes, result in liquid fractions that are easier to transport and/or to valorize.

As an example, after separating the possibly formed solids, the fraction of aromatic compounds can be separated, the gaseous fraction can first be treated in units allowing the oligomerization and/or the cyclization of acetylene, and then, after another gases/liquids separation, the residual gas fraction with a high ethylene content can be treated in Dimersol type units which produce ethylene oligomers.

The conversion of methane, even partially achieved, on the refining scene proper, into products which are easier to valorize, also shows considerable economical advantages.

Different methods for converting methane have already been suggested; for example, U.S. Pat. No. 4,199,533 describes a method allowing the production ethylene and/or ethane from methane, which consists of reacting chlorine with methane at a temperature higher than 700° C. This process has an important drawback since it involves the use of very corrosive gases such as chlorine and hydrochloric acid at high temperatures.

In addition, Patent FR-A-711,394 describes a process for transforming methane in which the heat necessary for the heating is obtained from starting points of a gas production process.

Patent FR-A-1,364,835 describes a process preventing side reactions in the hydrocarbon oxidation.

Note that the previous techniques are also illustrated by Patents WO-A-8,700,546 and DE-A-1,542,406.

Many processes for the catalytic cracking of methane have been described in the prior art, using for example zeolitic catalysts, as in Patent EP No. 93543, but all the catalysts used show a very short life, which is due to coke layers formed in the reaction.

The oxidizing coupling of methane is a well-known process which can be achieved either in the presence of oxygen or even in the absence of oxygen; in that case, metallic oxides intervene in the reaction by being reduced; U.S. Pat. Nos. 4,172,810, 4,239,658, 4,443,644 and 4,444,984 are examples for this type of processes. They are discontinuous since the metallic oxide must be regenerated.

Among the thermal cracking processes which can transform methane is the "Wulff process", that consists in using refractory contact masses; at first, the refractory mass is heated by air combustion of a fuel which can be the feedstock itself; then, the hydrocarbon to be cracked is decomposed by absorbing the heat accumulated by the refractory material during the previous period; it is thus a discontinuous process.

The electric arc and plasma processes are essentially directed to the preparation of acetylene; their high electric power consumption makes them difficult to exploit.

Another type of process, which is sometimes called autothermal, consists in burning a part of the feedstock in order to supply the cracking reaction with the necessary calories; this type of process uses a burner in which about ⅓ of the hydrocarbon is burnt, the rest being cracked. Considering the high temperatures that are employed, this type of process essentially produces acetylene and coke.

Patent FR No. 1,211,695 describes a combined process of hydrocarbon pyrolysis that consists of mixing methane with warm combustion gases which do not contain oxygen in excess, then in injecting into the obtained mixture paraffinic hydrocarbons with more than one atom of carbon; a very low amount of the methane can be transformed into acetylene with this process.

The dehydrogenating thermal coupling of methane is highly endothermic and requires the obtaining of a very high thermal flow density at high temperatures, from 1,100° to 1,500° C. It is necessary that the maximum heat supply is performed in the zone where the endothermic cracking and dehydrogenation reactions take place; besides, the obtaining of valorizable products such as acetylene, ethylene and/or aromatic compounds requires a very short contact time followed by a rapid quenching so that a "square" temperature profile can be obtained.

There is presently no industrial process available using a controlled heat transfer through a wall, so as to transform methane into easily valorizable hydrocarbons.

OBJECT OF THE INVENTION

The object of the present invention is to compensate for this deficiency and propose a process for thermally converting methane into hydrocarbons with higher molecular weights, as well as a reactor for the implementation of this process, leading to an easier, more flexible and better controlled production.

SUMMARY OF THE INVENTION

More particularly, the invention relates to a process for thermally converting methane into hydrocarbons with higher molecular weights in a ceramic reaction zone comprising a series of juxtaposed channels grouped in rows and covering at least a part of the length of said reaction zone, parallel to its axis, said channel rows being non adjacent to one another, the reaction zone also comprising on one hand a heating zone surrounding said channel rows either on said part of the reaction zone or on a part of the length of said reaction zone when said channels cover the whole length of the reaction zone, and, on the other hand, a cooling zone following said heating zone, comprising circulating a gas containing methane, for example a molar percentage of methane from 10 to 99% in the channels of said rows, heating the heating zone by supplying electric power through successive independent cross sections, substantially perpendicular to the axis of said reaction zone, substantially parallel to the plane of said rows and tight towards the channels of the reaction zone, introducing a cooling fluid into said cooling zone and collecting said hydrocarbons with higher molecular weights at the end of the reaction zone.

The reaction zone is the heating zone which heats the gaseous mixtures forming the feedstocks as well as the cooling zone (or quenching zone) which cools the effluents either indirectly through contact with a cold fluid on the walls of the channels or directly through the mixing of the effluents with a cold fluid.

More particularly, said heating zone is heated by supplying electric power with means such as an electric resistance for instance, which heats, by the Joule effect, the walls of the channel rows through which the gaseous mixtures circulate.

This type of static heating, as compared to a dynamic heating through circulation of a heat-conducting fluid surrounding channels conveying the gaseous reaction mixture, contributes towards an easier and especially better controlled implementation of the process.

The conversion rate of the process is thus increased and the selectivity improved.

According to one of the major characteristics of the invention, the electric resistances which supply the heating zone with heat are independently fed with electric power, either separately or in small groups, in order to define heating sections along the heating zone and be able to modulate the energy amount supplied in this whole zone.

The heating zone is generally composed of 3 to 20 heating sections, preferably 5 to 12. In the first part of this zone, the gas containing methane, which has been previously heated up to about 650° C., is generally quickly heated to a maximum temperature at most equal to 1,500° C., advantageously 1,000°-1,300° C. (the heating zone begins where the feedstock is introduced).

In the second part of the heating zone, which follows the first one, the electric power supplied to each heating section of this part is modulated so that the gases are maintained at a substantially constant temperature, close to the maximum temperature of the first part, in order to obtain a temperature profile which remains substantially even all along this second part.

The modulation of these heating sections is achieved in a conventional way; the resistance elements corresponding to the sections mentioned above are generally supplied by modulating units equipped with thyristors. Transformers can optionally allow to adapt the voltages a priori, whereas the modulators allow to perform the fine and continuous regulation of the injected power.

In order to adjust the whole system, the channels in which the feedstock circulates are, for example, fitted, at the level of the heating zone and preferably at the level of maximum heating, with at least one sheathed pyrometer with a thermocouple, suited to the temperature level, as for example chromel-alumel or Pt/Pt Rh. These thermocouples are control thermocouples which transmit their information to the regulator that operates the thyristor modulator.

In the first part of the heating zone, the electric power is almost exclusively used for bringing the reaction mixture from its initial temperature—about 650° C.—to a temperature of 1,200° C. for example, around which the dehydrogenating endothermic coupling reactions occur. It is thus at the beginning of the second part of the heating zone that it becomes necessary to supply the reaction medium with the maximum power, which can be easily done by modulating one or several heating sections.

The length of the first part of the heating zone generally represents from 5 to 50% of the total length of the heating zone, advantageously 10 to 30%, and preferably 15 to 25% of this zone.

The electric power provided in this first part of the heating zone is such that it generates a high temperature gradient, generally from 5° to 60° C./cm, advantageously 10° to 30° C./cm.

In the second part of the heating zone, the electric power which is supplied is modulated at the different heating sections in this zone so that the temperature variation remains low in the zone, generally lower than about 20° C. (+ or − 10° C. around the fixed value) and advantageously lower than about 10° C.

The length of the heating zone generally ranges from 50 to 90% of the length of the total reaction zone.

With the heating conditions described above, a high rate of heat transmission is obtained at a high temperature level.

The space defined between the rows of channels conveying the feedstock can be occupied by a second series of channels also determining at least one file of channels alternately with those conveying the gaseous mixture. These channels are generally divided into at least two parts not communicating with one another and with the channels conveying the charge.

According to a first embodiment of the heating zone, the space in the reactor between the plates reserved for the feedstock conveyance can be filled with at least one plate generally substantially similar to the plate of the conveying channels, the second series channels of which are substantially perpendicular to the channels conveying the charge. The heating elements are housed in the second series channels.

According to another embodiment of the heating zone, the second series channels can be substantially parallel to the circulation channels. The heating means are then substantially parallel to the plane of the circulation channel plates but in a direction substantially perpendicular to the axis of the channels. The side walls of the second series channels are therefore hollowed out in order to allow them to pass and in order to determine independent heating sections substantially perpendicular to the direction of the feedstock flow.

The unitary plates serving to convey the gases of the process are preferably identical to one another. It is also preferable that the plates in which the heating elements are placed are similar to one another; they can be different from the plates conveying the gases.

The heating zone is followed by a cooling zone (or quenching zone) so that the temperature of the effluents in the heating zone can be decreased very rapidly down to about 300° C. for example.

According to an embodiment, with an indirect quenching, the channels conveying the feedstock generally cover the whole length of the reaction zone. The second series channels, the length of which is substantially equal to that of the first ones, are divided in at least two parts which do not communicate with one another and with the channels conveying the feedstock. The first part (inlet side) corresponds to the heating zone and the second part (effluent outlet side) corresponds to the cooling or quenching zone, from which a cooling fluid flows out, generally parallel to the feedstock flow.

Within the scope of the invention, the continuous heating reactor and quenching exchanger unit can be achieved either in the form of a monoblock or by jointly juxtaposing unitary elements of the same form, which are assembled together by any appropriate means, for example with flanges. The use of ceramic withstanding temperatures higher than 1,150° C., and more particularly silicon carbide, which is an easily extrudable material, facilitates the implementation of such units or unit elements.

According to one embodiment of the invention, the cooling fluid inflow in the rows of channels constituting the second section and used for conveying the fluid is substantially perpendicular to the axis of these channel rows, owing to an opening in one of the lateral walls of the concerned channels located on the periphery; the channels of the same file are linked at the level of the cooling fluid inlet by means of openings made in their lateral walls, so that the total channels assigned to this purpose are crossed by the fluid.

Numerous ceramic indirect heat exchangers have been described previously; they are essentially used for turbine motors, where the material of the exchanger must be able to withstand temperatures from 1,200° to 1,400° C. French patent No. 2,436,956, U.S. Pat. No. 4,421,702, Japanese patent application Nos. 59,046,496 and 59,050,082 and French patent Nos. 2,414,988 and 2,436,958 (additional to the previous patent) can for example be cited, the latter describing a process for manufacturing a ceramic indirect heat exchange element which can be advantageously used within the scope of the invention, after some modifications have been carried out.

The fluids which can be used for cooling the effluents at the level of the indirect quenching zone can be for example air, alone or mixed with combustion fumes or low-temperature water steam under low pressure.

According to another embodiment, in the case of a direct quenching reaction, the channels conveying the feedstock generally extend over a part of the total length of the reaction zone and the space defined between these channel rows is reserved for the heating zone, the length of which is substantially equal to the length of the channels through which the feedstock goes.

The reaction effluents which leave the heating zone are very rapidly cooled by injection and direct contacting in these effluents, for example with at least one ceramic injector located on the reactor periphery and cooling fluids such as liquefied petroleum gases, propane or hydrocarbon oils, propane being a preferred quenching gas because it can also be partially cracked and then contribute towards the forming of products such as ethylene.

The use of ceramic materials, preferably silicon carbide, allows wall temperatures which can reach 1,500° C. in continuous use, which exceeds the limits of metallurgy in its present stage and allows an increase in the rate of heat transmission and the reaction temperature.

Furthermore, the use of the different transverse heating sections, independent from one another, at the level of the second part of the heating zone, permit a maximum thermal energy to be located at the place where the most part of endothermic cracking reactions take place, and to maintain an substantially uniform temperature in the rest of the heating zone.

These characteristics, together with the high value of the exchange surface (S)—reaction volume (V) ratio, which generally ranges from 200 to 1,000 $m^{-1}$, permit, according to this process, a heat conversion of methane into acetylene, ethylene and benzene products which takes place with a good conversion rate and a high selectivity.

The hydrocarbon feedstocks which can be used within the scope of this invention are gaseous in the normal temperature and pressure conditions, with a usual methane molar percentage from 10 to 99%, for example 20 to 99% and preferably 30 to 80%.

The rest of the feedstock can be composed of aliphatic hydrocarbons, saturated or not, with a number of carbon atoms of at least two, such as, for example, ethylene, ethane, propane or propylene; other gaseous constituents of the feedstock can be nitrogen, carbon dioxide or carbon monooxide or, preferably, hydrogen, the presence of which allows to reduce the forming of coke. The hydrogen molar proportion can range from 1 to 90%.

It is possible, within the scope of this invention, to add dilution water (steam) to the feedstocks defined above; the dilution water (steam): hydrocarbon feedstock ratio by weight ranges from 0.1 to 1.

The feedstocks to be treated generally remain in the reaction zone for a time ranging from 2 to 1,000 milliseconds, preferably 30 to 300 milliseconds.

The invention also relates to the device for implementing the process. This device can also be used for any steamcracking process of a hydrocarbon with at least two carbon atoms.

More particularly, the invention relates to a device containing gaseous mixture supply means and discharge means for the produced effluents, comprising an elongate reactor 1, preferably with a square or rectangular section, made of ceramic, with an axis of symmetry, connected on one hand to a first end, to said supply means, and on the other hand, to the opposite end, to said discharge means, said reactor being fitted with a series of juxtaposed channels 11, grouped in rows, adapted to the circulation of the gaseous mixture and extending over at least a part of said reactor length, parallel to its axis, said channel rows forming multiple plates 4 which are not adjoining one another and which define tight spaces 17 between said plates, said reactor also comprising in a first zone (first end side) electric heating means 5, 22 in each said space suited for heating said channel plates through successive dependent transverse sections which are substantially perpendicular to the axis of said reactor and substantially parallel to the plane of said plates, said heating means thus substantially surrounding said channel plates 4, either on said reactor part or on a part of the length of said reactor 1 when said channels 11 extend over the whole length of the reactor, said reactor also comprising heating servocontrol and modulation means 7, 8 connected to said heating means, said reactor also comprising in a second zone (opposite end side) which is contiguous to but does not communicate with the first zone, effluent cooling means adapted for cooling either channel plates 4 by circulating a cold fluid in said tight spaces in the second reactor zone (indirect quenching) or the effluents leaving said channels 11 by direct contact (direct quenching).

Each plate generally forms at least one file of unitary channels but, according to a particular embodiment of the process, each unitary channel can be subdivided into multiple smaller elementary channels.

The total number of channel rows is not a determining factor in the process; it is obviously dependent on the dimensions of the whole heating reactor, quenching device and unitary channel dimensions. Moreover, both external channel or space rows are, within the scope of this invention, preferably taken up by the heating or cooling means.

The number of unitary channels per file is neither a determining factor and depends on the total dimension of the whole and on the dimension of one unitary channel.

The section of a unitary channel generally ranges from 9 to 900 mm$^2$, advantageously from 25 to 100 mm$^2$. The section can have any form but it is preferably square or rectangular. The length of a channel varies according to the feedstocks to be treated, the process temperature and the desired contact time. The unitary plates are generally parallelopipedic. It is preferable, within this invention, that the unitary plates which are used show the same geometry and an identical number of unitary channels.

Any material showing a satisfactory electric conductibility can be used in the form of an electric resistance within the scope of the invention, providing that it is stable at a temperature of 1,500°–1,600° C., for example molybdenum and nickel-chromium alloys.

The plates, be they unitary or grouped in rows, are made of a refractory material; ceramics such as mullite, iolite, silicon carbide, silicon nitrides, silica or alumina can be used; silicon carbide is preferably used because it has a relatively high heat conductivity and can be extruded.

The distance between the rows of channels (or plates) which define the spaces designed to receive the heating means or the cooling fluid generally ranges from 1 to 150 mm, advantageously from 3 to 100 mm. The distance between the various electric heating elements generally goes from 1 to 200 mm, according to the axis of the reaction zone.

With a distance advantageously ranging from 3 to 50 mm, a very good temperature stability has been reached in the maximum heating zone (substantially constant temperature zone).

The invention also relates to the construction of the ceramic device for the implementation of the process.

In the first reactor zone, a plate of channels 11 from one series and a plate of channels 28 from a second series are alternately juxtaposed following a substantially adjacent way, heating sections are determined in said plate of channels 28 by introducing heating means 5, 22 substantially parallel to the plane of said plates, either in the direction of channels 28 from the second series or in a direction substantially perpendicular to said channels 28, said heating means 5, 22 being connected to said heating servocontrol and modulation means 7, 8, said plates of channels 11 and 28 being juxtaposed so that channels 11 from the first series are substantially perpendicular to said sections; if need be, the plate containing said heating means is isolated from said plate of channels 11; in the second reactor zone, either a direct cooling means, preferably close to the outflow of channels 11 effluents, or an indirect cooling means for channels 11 is introduced, following which a plate of channels 11 adapted to receive the effluents in the continuation of channels 11 from said first zone and a plate of channels 18 substantially parallel to channels 11 and adapted to circulate a cooling fluid are juxtaposed in an alternate and substantially adjacent way; if need be, said plate of channels 18 is isolated with a partitioning 32.

In the case of indirect cooling, a tightness system is set up between the two parts of the reactor by means such as ceramic flanges.

The use of ceramic and more particularly of silicon carbide, which is an easily extrudable material, facilitates the achievement of such wholes or elements of wholes.

BRIEF DESCRIPTION OF THE DRAWINGS

It will be easier to understand the invention with the figures which illustrate in a non limiting way the various embodiments of the process, among which:

FIG. 1A represents a longitudinal section of the reactor with direct quenching and FIG. 1B represents a view of the reactor with indirect quenching, FIG. 2 represents a cross section of the reactor according to one particular embodiment, and FIGS. 3 and 3A show the heating zone.

DETAILED DESCRIPTION OF DRAWINGS

FIG. 1A represents, according to an embodiment, a vertical reactor 1 or direct quenching reaction zone, with an elongate form and a square section, comprising a distributor 2 allowing to supply the reactor to be supplied with the gaseous reaction mixture through an inlet opening 3. The gaseous reaction mixture contains for example 50% of methane and has been preheated in a conventional preheating zone which does not appear on the figure and which is preferably a convection preheating. The reactor is a multiconduit type one with a square section. It has multiple parallelopipedic unitary plates 4 which are substantially parallel towards one another and form rows of channels 11 that are substantially parallel towards one another and through which the gaseous reaction mixture flows. These plates of channels are generally not adjoining and form spaces 17 in which the heating means 5, 22 of the electric resistances are for example located; the latter, which are described hereunder, substantially surround the various plates of channels and are tightly isolated from the feedstock and the reaction effluents by partitionings 14. The heating zone 9 in which the heating means 5, 22 are housed is fit up so that transverse heating sections 6 are constituted, which are substantially perpendicular to the reactor axis defined according to the feedstock flow direction (horizontal sections in the case of FIG. 1). These sections are generally independently heated and electrically supplied with a pair of electrodes (15a, 15b, FIG. 2).

Heating zone 9, the length of which represents for example 90% of the reactor, is fit up so that, in its first part (inlet side), the channels conveying the gaseous mixture are heated up to a temperature of 1,200° C., following a thermal gradiant of 20° C. per centimeter. To that end, at least one pyrometric probe 8 fitted with a thermocouple, for example chromel-alumel, is housed in at least one channel 11 conveying the feedstock, preferably substantially at the level of the heating zone with the maximum temperature and the probe transmits information to a regulator 7a which operates for example a modulator 7b fitted with a thyristor and connected to the electric resistances 5. The power supplied to each heating section is thus conventionally modulated according to the temperature of each section.

The gaseous mixture then continuously flows through the channels 11 which are in contact with the second part of the heating zone, where the temperature is usually kept at a substantially constant value, substantially equal to the temperature reached in the end of the first heating zone, that is, in the case cited above, 1,200° C. To that effect, the electric power is modulated, by means of one or several probes 8 preferably housed along the second heating zone and following the same regulation pattern as above, according to the temperature along said zone of maximum heating, where most endothermic reactions take place, so that the temperature variation in relation to the point fixed is lower by about 5° C. in relation to the value fixed.

This second zone of maximum heating corresponds to about 80% of the total heating zone; it ends with a tight partitioning 14 which can for example be made of refractory cement in order to avoid any gas effluent and/or cooling fluid inflow from the following cooling zone.

At the outlet of the heating zone, the reaction effluents leave channels 11 and are cooled in a cooling zone 10. They are contacted with a quenching agent such as propane, introduced through quenching injectors 12 located on the periphery of reactor 1 and connected to an exterior propane source (not represented on FIG. 1). The total effluent gases and propane are cooled to a temperature of about 500° C. and gathered through an outlet opening 13 at the end of reaction zone 1.

According to another embodiment with an indirect quenching reactor represented in FIG. 1B, the rows of channels 11 conveying the gaseous reaction mixture extend continuously all over reactor 1. Their length is substantially equal to that of the reactor.

The heating zone in contact with the channels represents for example 60% of the total reactor length. The rows of channels 11 conveying the feedstock are first heated under the upper part (inlet side) in the same conditions as those described above for FIG. 1A, then cooled in the lower part by the cooling fluid which flows through space 18, between the plates of channels 11, cooling the walls of the effluent flow channels.

The obturation of channels 17, 18 with a tight obturation device 14 defines and insulates the heating zone 9 from the cooling zone 10. Another tight obturation 32 avoids the mixing of the hydrocarbon effluents with the cooling fluid.

The inflow of the cooling fluid into this space, for example in the rows of channels 18 intended to convey it, can be substantially perpendicular to the axis of these rows of channels, through an opening 16a in one of the lateral walls of the concerned channels located on the periphery; the channels of the same file are generally connected at the level of the cooling fluid inlet, through openings in their lateral walls, so that the total channels intended to this use are crossed by the cooling fluid. The withdrawal of the cooling fluid can also take place substantially perpendicularly to the axis of these rows of channels.

The cooling fluid preferably enters the quenching zone 10 through openings 16a connected to a line 19 and located near the partitioning 14. It flows across spaces 18 which are channels parallel to the channels 11 conveying the feedstock, with substantially the same dimension, in the direction of the reaction effluents, and leaves reactor 1 through openings 16b connected to line 20.

If the case arises, the flow direction of the cooling fluid can be reversed; it enters then the quenching zone 10 through line 20 and, after cooling the reaction effluents counter-currently, leaves zone 10 through line 19.

The reaction effluents which have thus been cooled at a temperature of about 300° C. are collected at the end of channels 11 and gathered at the outlet opening 13 through collecting line 21, as in FIG. 1.

If need be, according to the nature of the feedstocks to be treated, another particular embodiment consists in carrying out a two-stage cooling, the first stage being achieved by indirect quenching in the interplates space down to a temperature from 500° to 700° C. and the second stage being made of a cooling through injection of the cooling fluids into the effluents of the indirect quenching zone. A direct quenching down to a temperature of about 500° C. can also be achieved, followed by the cooling of the effluents down to about 200° C. with a heat exchanger.

Different ways of producing the reactor for the implementation of the process according to the invention are described hereunder, which only illustrate the heating zone, the quenching zone being direct or indirect as described above with FIGS. 1A and 1B.

FIG. 2 shows a way of achieving a vertical and elongate reactor 1, following a horizontal section.

Reactor 1 is achieved by juxtaposing in a non adjacent way the unitary plates 4a, 4b, 4c, ... , which are placed vertically, each of them containing a file of unitary channels 11. An electric conductor tape 5 in an insulating casing is placed in space 17, between the walls of two successive plates, so that it substantially surrounds each plate 4a, 4b, 4c, thus defining at least partially a heating section.

Electrodes 15a and 15b allow the electric supply of this heating tape in an independent way. Reactor 1 is thermally insulated by insulator 25 and located in a frame 26. In order to minimize the power losses, the tape can stick to the walls of the next plates 4b, 4c, so that the inter-plate space 17 can be smaller than the dimension of a unitary channel.

According to another embodiment illustrated by FIG. 3, the space 17 in reactor 1, between plates 4 of channels 11 reserved for the feedstock flow, is filled with at least one plate substantially identical to plate 4, the channels 28 of which, with substantially the same dimension, are placed substantially perpendicularly to channels 11, so that the unitary plates with channels alternately set in a vertical and a horizontal position, thus successively placed in an orthogonal way towards one another, are juxtaposed. Inside channels 28 (FIG. 3), resistant metallic elements 27 are to be found, in the form of wires, spirals or tapes made of molybdenum, substantially parallel to the plane of plates 4. Channels 28 are advantageously filled with heat-conducting ceramic powder such as CSi and are obturated by a ceramic cement 31, and, at their ends, electrodes 15a and 15b protrude. With such a layout, the partitioning at both ends of the heating zone is achieved by the walls of channels 28.

According to another embodiment, illustrated by FIG. 1B, the space 17 between the plates 4 of channels 11 is filled with at least one plate substantially identical to plate 4, the channels 28 of which have substantially the same dimensions and are substantially parallel to channels 11. The different plates are placed substantially parallel to one another. In each plate of channels 28, multiple heating resistances 22 made of silicon carbide in the form of bars or cylinders (Kanthal resistances, registered trademark) are set substantially parallel to one another and following a plane substantially parallel to the plates, so that their largest dimension is substantially perpendicular to the axis of channels 11. To this end, the walls of channels 28 are laterally hollowed out, to allow their appropriate positioning in the various sections of the heating zone.

The opposite ends of the heating zone are obstructed by ceramic cement partitionings 14 to avoid the inflow of the feedstock and of the reaction effluent—cooling fluid mixture into the heating zone in the case of a direct quenching reactor and to avoid the inflow of the feedstock and of the cooling fluid in the case of an indirect quenching reactor.

These embodiments are of course described for information only, in a not limiting way. It is possible to change the various heating means described above and to adapt them to the different configuration examples of the heating zone. For example, the Kanthal resistances can be used for the embodiment shown in FIG. 3, where the resistances can be sustained by appropriate ceramic hangers or bearers.

There is also an improved form of implementation of the process according to the present invention.

According to this embodiment, the effluent of a plasma flare fed with a plasmagene gas is added to the preheated gas containing methane which constitutes the process reagent. It is well-known that, by passing a gas known as plasmagene through an electric arc, a particular reaction medium is created, which is electrically neutral but rich in ions, electrons, atoms and/or wound molecules. The plasmagene gas can be for example hydrogen, argon, water steam, nitrogen, methane or any other usual gas, or the mixture of several of them in variable proportions. It can particularly be the total or part of the gas supplying the heating zone.

According to a preferred embodiment of the invention, a part of the gas that constitutes the feedstock can be branched off, before or after reheating, preferably afterwards, and supplied to the plasma flare. The flare effluent is immediately injected into the reactive fluid remainder, just before the inflow into the pyrolysis zone.

To this end, 1 to 20% of the feedstock can be used, but a continuous source of plasmagene gas can also be employed. The effect of this dilution with plasma is to favor the initial heating stages and, thus, to highly facilitate the conversion of methane into hydrocarbons with higher molecular weights.

It becomes thus possible to work with a lower temperature than in the case where there is no dilution, that is, for example, an average reactor temperature lower by about 100° C.

Although the heat level is lower, the methane transformation ratio is maintained. On the other hand, the tendency to produce acetylenic compounds is reduced whereas the tendency to produce olefinic and aromatic compounds is increased.

With this reserve, the average heating temperature most often ranges from 600° to 1,300° C. The purpose of the quenching step is to bring the temperature of the mixture down to less than 400° C., for example 100°–350° C. or lower.

Still further an even more improved embodiment of the process has been discovered.

According to this embodiment, the implementation of which is easy, at least one priming reagent selected from the group formed by oxygen, ozone and hydrogen peroxide is added to the preheated gas, in a convenient proportion compared to the reagent amount in the reaction zone.

The priming reactor is introduced into the preheated gas mixture, preferably in a relatively low amount in relation to methane, before the introduction of the reaction mixture into the heating zone.

Without referring to any theory, one may think that the priming reagent, which has been introduced into the preheated feedstock preferably at less than 300° C. and generally at 500°–600° C., favors the formation of radicals, particularly methyl radicals, and thus also favors the starting of the conversion reaction of methane at a lower temperature, which results in a higher yield for the sought products: ethylene and aromatic products.

It is therefore not advisable to have too great an amount of priming reagent, because this might lead to the formation of a considerable quantity of radicals and to an excessive formation of secondary products, especially carbon oxides (CO, $CO_2$).

The amount of priming reagent introduced into the preheated gas mixture, expressed in percentage of gram atoms of introduced oxygen in relation to the amount of methane expressed in mol, generally ranges from 0.01 to 10%, preferably from 0.1 to 1%.

According to a preferred embodiment of the invention, the priming reagent is substantially pure oxygen (that is to say, which less than 1% by volume of impurity), or oxygen diluted with an inert gas such as, for example, nitrogen or argon, or else a more complex gas mixture containing oxygen, such as for example air, or air enriched with oxygen or air diluted with an inert gas. It is also possible to introduce the priming reagent by diluting it beforehand in a part of a gaseous mixture to be treated.

If the gas that is used is ozone, the latter can be employed in a substantially pure form or diluted in a gas as mentioned above for oxygen. A mixture of oxygen and ozone or ozonized air can be used.

If hydrogen peroxide is used, the latter can be employed in a substantially pure form or diluted. It is also possible to use aqueous hydrogen peroxide, sometimes also called oxygenated water, providing that the water amount which is introduced into the reactor remains within the limits described above.

It is possible to preheat the priming reagent before introducing it, for example up to a temperature of 150° C.

The effect of introducing at least one priming reagent is to highly favor the transformation of methane into hydrocarbons with a high molecular weight. The introduced quantities being relatively low, only a small proportion of carbon oxides is formed. This slight loss is widely compensated for by the beneficial priming effect of the reaction, which permits working with lower temperatures and shorter residence times in the reaction zone for the feedstock to be treated.

It is therefore generally possible in this case to work with an average temperature in the pyrolysis reactor of about 70° to 100° lower compared to the case without introduction of a priming reagent. The time in the reaction zone can also be slightly shortened by using a priming reagent.

EXAMPLE

An indirect quenching reactor made of silicon carbide is used. The length of the reaction zone, which represents the length of the unitary channels conveying the feedstock, is 3 m. The heating zone is heated by Kanthal electric resistances made of ceramic which are inserted between the plates of unitary channels and placed in such a way that their largest dimension is perpendicular to the axis of the unitary channels.

The heating zone comprises two adjacent parts; in one part, with a length of 0.5 m, the feedstock, which has been preheated at 600° C., is brought up to 1,200° C.; this zone, with a high thermal gradient of 12° C./cm, is thermally regulated by thermocouples located in the unitary channels. In the second part, which has a length of 1.5 m, the feedstock is maintained at 1,200° C., more or less 10° C., with the thermal regulation of five heating sections comprising five resistances each, by means of five thermocouples located in the channels. The quenching zone, which is 1 m long and is supplied with air as a cooling fluid, is an extension of the heating zone. At the outlet of the quenching zone, the reaction effluents have a temperature of 250° C.

The feedstock which is used is natural gas, the heaviest fractions of which (LPG) have been removed by compression and cooling at −100° C.; the remaining fraction, which essentially comprises methane and ethane, is diluted with hydrogen in order to obtain the feedstock to be used, its molar composition being the following:

| Compound | Mols |
|---|---|
| $H_2$ | 100 |
| $CH_4$ | 100 |
| $C_2H_6$ | 5 |

This mixture is heated up to 600° C. and cracked in the reactor described above, following the cited operating conditions; it remains in the heating zone for 200 ms.

After cooling at room temperature, the gases, the liquids and the solids are separated.

With 205 mols of the mixture which is used, the following products are obtained:

| Products | Amount |
|---|---|
| $H_2$ | 170.25 mols |
| $CH_4$ | 50 mols |
| $C_2H_2$ | 6.25 mols |
| $C_2H_4$ | 15.0 mols |
| Benzene | 1.5 mol |
| Liquid phase without benzene | 104 g |
| Coke | 6 g |

We claim:

1. A process for thermally converting methane into hydrocarbons with higher molecular weights in a ceramic reaction zone having an axis and provided with parallel rows of channels extending over at least a part of the total reaction zone said channels being lengthwise parallel to said axis and to each other, said rows of channels being spaced from one another, the reaction zone also comprising a heating zone in indirect heat exchange contact with said rows of channels and a cooling zone which is an extension of said heating zone and is in indirect heat exchange contact with said rows of channels, comprising circulating a gas containing methane in the channels of said rows, heating the heating zone with an electric power supply through successive, independent transverse sections which are substantially perpendicular to the axis of said reaction zone and in indirect heat exchange contact with the channels of the reaction zone, so that a first part of the heating zone is maintained at a maximum temperature above 650° C. to at most 1,500° C., at a temperature gradient ranging from 5° C./cm to 60° C./cm on a length from 5 to 50% of the total heating zone length, and wherein a second part of the heating zone, following said first part is heated at substantially said maximum temperature so that the temperature variation all along said second part is less than about 20° C., and said circulated gas is heated to the maximum temperature introducing a cooling fluid into said cooling zone and collecting said hydrocarbons with higher molecular weights at the end of the reaction zone.

2. A process according to claim 1, wherein said cooling zone comprises a second series of channels alternating with those conveying the gas containing methane, and wherein said cooling a fluid is introduced and withdrawn substantially perpendicularly to the axis of the channels of the second series.

3. A process according to claim 1, wherein the cooling fluid is directly contacted with effluents resulting from the heating of the gas, whereby said hydrocarbons with higher molecular weights are collected and mixed with said cooling fluid.

4. A process according to claim 1, wherein the gas also contains hydrogen.

5. A process according to claim 1, wherein the collected hydrocarbons with higher molecular weights at the end of the reaction zone comprise a substantial portion of ethylene.

6. A process according to claim 1, wherein the maximum temperature is 1,000°–1,300° C.

7. A process according to claim 1, wherein the temperature variation in the second part of the heating zone is less than about 10° C.

8. A process according to claim 1, wherein the temperature gradient is 10°–30° C./cm.

9. A process according to claim 1, wherein the length of the first part of the heating zone is 10–30% of the total length of the heating zone.

10. A process according to claim 1, wherein the length of the first part of the heating zone is 15–25% of the total length of the heating zone.

11. A process according to claim 1, wherein the residence time of the gas in the reaction zone is 2–1,000 milliseconds.

12. A process according to claim 1, wherein the residence time of the gas in the reaction zone is 30–300 milliseconds.

13. In a process for thermally converting methane to hydrocarbons having higher molecular weights, the step of passing a gas containing methane through an elongated heating zone, wherein in a first part of the heating zone, the gas is heated up to a maximum temperature above 650° C. to at most 1,500° C., at a thermal gradient ranging from 5° C./cm to 60° C./cm on a length from 5 to 50% of the total heating zone length, and wherein in a second part of the heating zone, subsequent to said first part, the gas is heated at substantially the maximum temperature with a temperature variation all along said second part lower than about 20° C.

14. A process according to claim 13, wherein the collected hydrocarbons with higher molecular weights at the end of the reaction zone comprise a substantial portion of ethylene.

15. A process according to claim 13, wherein the maximum temperature is 1,000°–1,300° C.

16. A process according to claim 13, wherein the temperature variation in the second part of the heating zone is less than about 10° C.

17. A process according to claim 13, wherein the temperature gradient is 10°–30° C./cm.

18. A process according to claim 13, wherein the length of the first part of the heating zone is 10–30% of the total length of the heating zone.

19. A process according to claim 13, wherein the length of the first part of the heating zone is 15–25% of the total length of the heating zone.

20. A process according to claim 13, wherein the residence time of the gas in the reaction zone is 2–1,000 milliseconds.

21. A process according to claim 13, wherein the residence time of the gas in the reaction zone is 30–300 milliseconds.

22. A process according to claim 13, further comprising the steps of preheating the gas containing methane prior to passing said gas through said elongated heating zone, and adding a plasmagene gas to resultant preheated methane.

23. A process according to claim 13, comprising the further steps of preheating said gas containing methane prior to passing said gas through said elongated heating zone, and adding to resultant preheated gas containing methane, at least one priming reagent selected from the group consisting of oxygen, ozone and hydrogen peroxide.

* * * * *